United States Patent [19]
Koenig, Jr. et al.

[11] Patent Number: 5,135,502
[45] Date of Patent: Aug. 4, 1992

[54] SOLID INTRODUCER FOR CATHETER TO A PORT AND METHOD OF USE

[75] Inventors: Marvin E. Koenig, Jr., Roseville; Robert Lee, Plymouth; Melvin B. Moschler, Jr., Britt, all of Minn.

[73] Assignee: Medfusion Inc., Ohio

[21] Appl. No.: 492,214

[22] Filed: Mar. 13, 1990

Related U.S. Application Data

[63] Continuation of Ser. No. 157,517, Feb. 18, 1988, abandoned, which is a continuation-in-part of Ser. No. 128,046, Dec. 3, 1987, abandoned.

[51] Int. Cl.$^5$ ............................................. A61M 5/00
[52] U.S. Cl. .................................. 604/164; 604/165; 604/110; 604/263; 604/175
[58] Field of Search ...................... 604/110, 164–166, 604/169, 170, 174, 175, 177, 178, 198, 263; 606/108

[56] References Cited

U.S. PATENT DOCUMENTS

| | | | |
|---|---|---|---|
| 2,001,638 | 5/1935 | Tornsjo | 604/165 |
| 3,063,345 | 11/1962 | Kowalk . | |
| 3,566,874 | 3/1971 | Shepherd . | |
| 3,595,230 | 7/1971 | Suyeoka | 604/164 |
| 3,598,127 | 8/1971 | Wepsic . | |
| 3,630,198 | 12/1971 | Henkin | 604/170 |
| 3,792,703 | 2/1974 | Moorehead . | |
| 3,875,938 | 4/1975 | Mellor | 604/169 |
| 3,995,623 | 12/1976 | Blake et al. . | |
| 4,072,146 | 2/1978 | Howes . | |
| 4,257,416 | 3/1981 | Prager | 604/250 |
| 4,377,165 | 3/1983 | Luther et al. . | |
| 4,406,656 | 9/1983 | Hattler et al. . | |
| 4,540,411 | 9/1985 | Bodicky | 604/169 |
| 4,569,675 | 2/1986 | Prosl et al. | 604/175 |
| 4,573,981 | 3/1986 | McFarlane | 604/263 |
| 4,643,199 | 2/1987 | Jennings, Jr. et al. | 604/198 |
| 4,655,751 | 4/1987 | Harbaugh | 604/198 |
| 4,668,221 | 5/1987 | Luther . | |
| 4,676,783 | 6/1987 | Jagger et al. | 604/198 |
| 4,702,739 | 10/1987 | Milorad | 604/198 |
| 4,747,831 | 5/1988 | Kulli | 604/198 |
| 4,762,516 | 8/1988 | Luther et al. | 604/198 |
| 4,846,805 | 7/1989 | Sitar | 604/198 |
| 4,850,961 | 7/1989 | Wanderer et al. | 604/198 |
| 4,944,725 | 7/1990 | McDonald | 604/164 |
| 4,944,728 | 7/1990 | Carrell et al. | 604/110 |
| 4,950,252 | 8/1990 | Luther et al. | 604/164 |

FOREIGN PATENT DOCUMENTS

| | | |
|---|---|---|
| 0008451 | 3/1980 | European Pat. Off. . |
| 1131865 | 10/1986 | United Kingdom . |
| 88/3035 | 5/1988 | World Int. Prop. O. . |

*Primary Examiner*—Stephen C. Pellegrino
*Assistant Examiner*—Ralph A. Lewis
*Attorney, Agent, or Firm*—Wood, Herron & Evans

[57] ABSTRACT

Apparatus for accessing the circulatory system of a person or animal includes a port and a device for accessing the port. The access device has a solid introducer with a catheter received thereabout. The introducer and catheter are covered by telescoping containers which expose the insertion ends of the introducer and catheter only at the time of insertion.

16 Claims, 7 Drawing Sheets

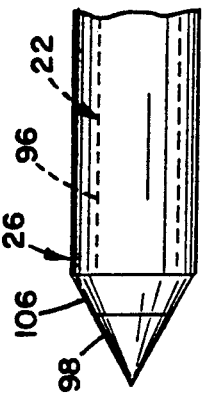
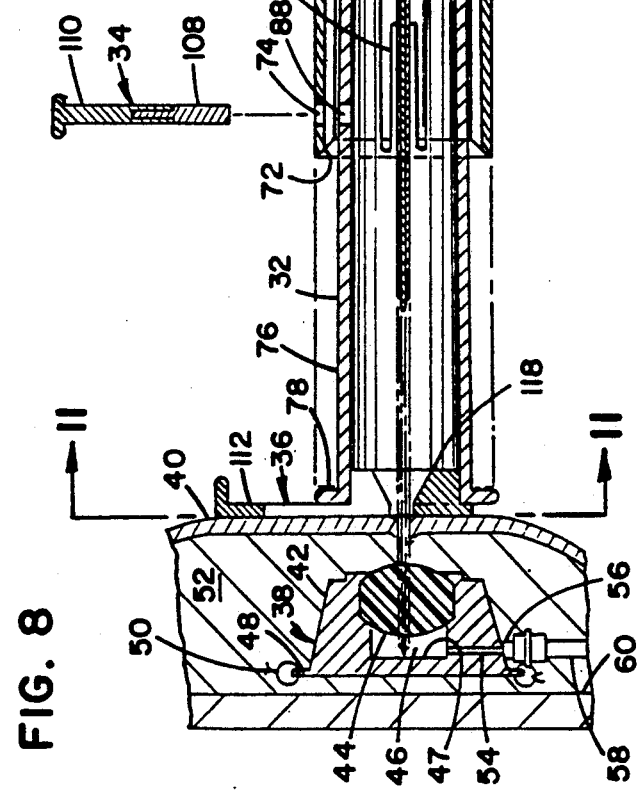
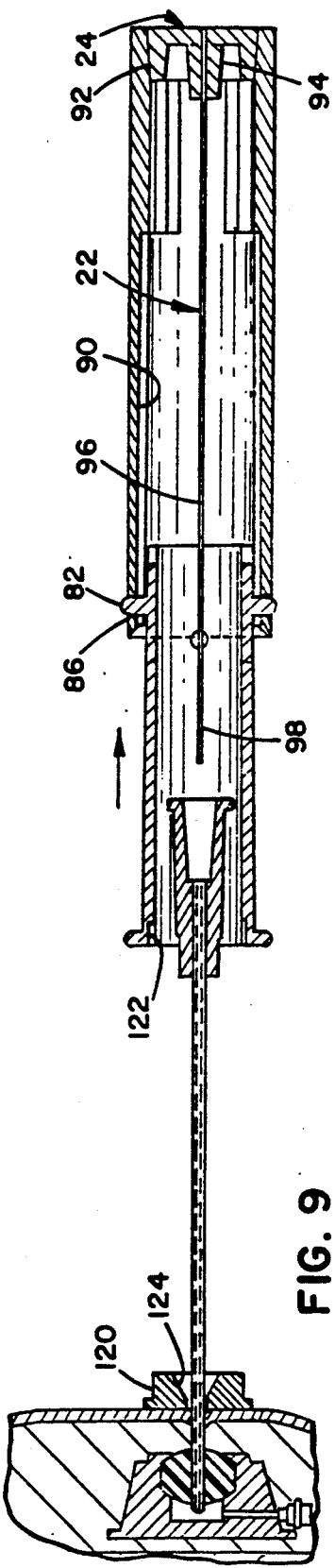
FIG. 10
FIG. 8
FIG. 9

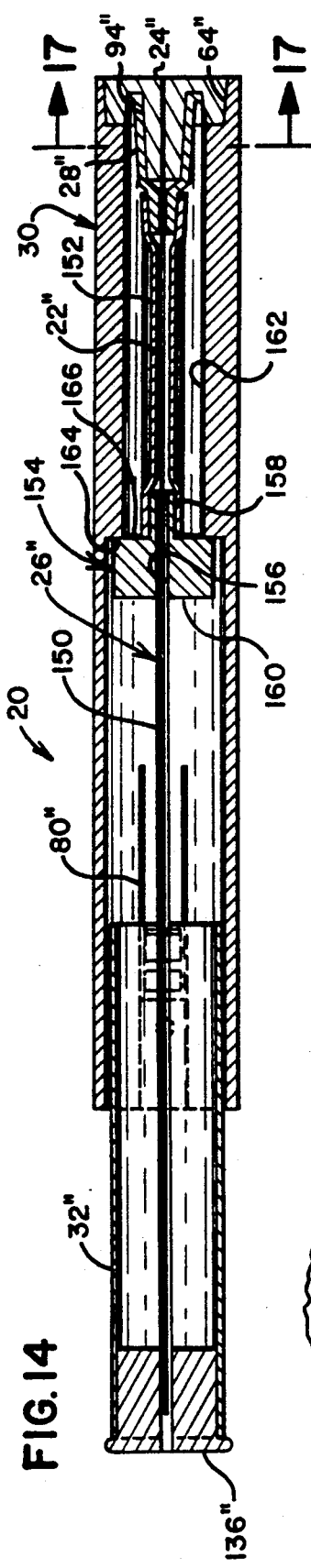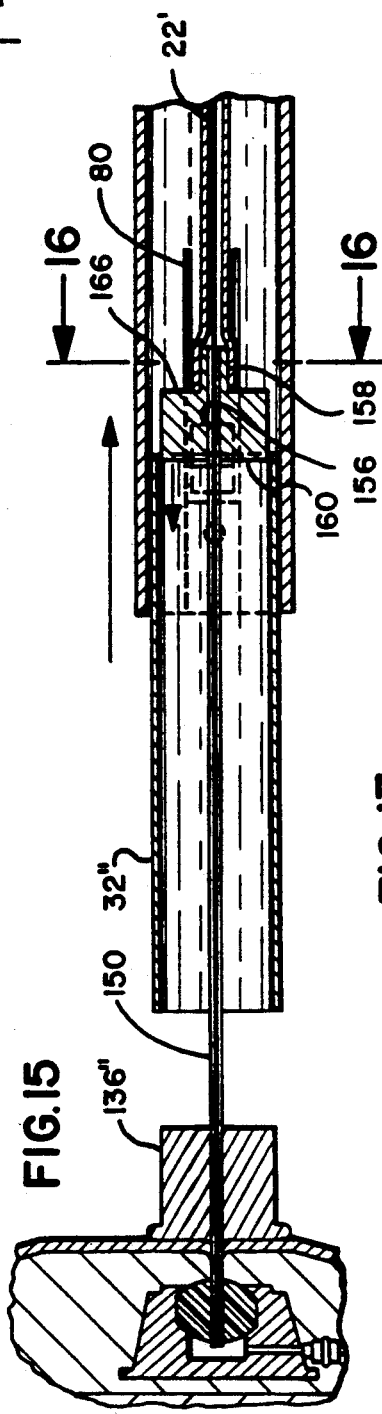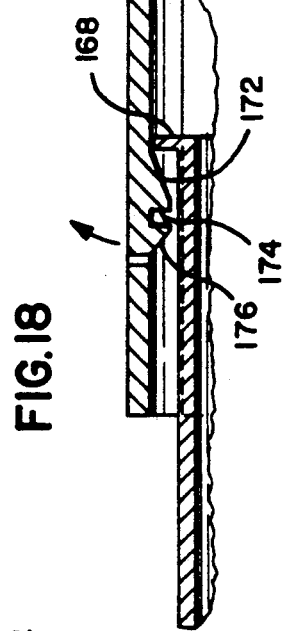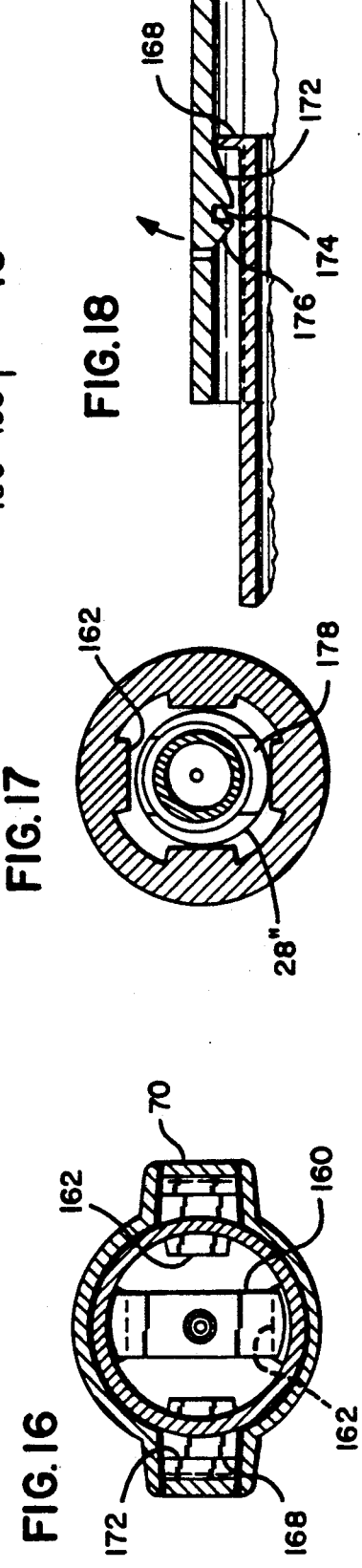

SOLID INTRODUCER FOR CATHETER TO A PORT AND METHOD OF USE

This is a continuation, of application Ser. No. 07/157,517, filed Feb. 18, 1988, now abandoned which is a continuation-in-part of application Ser. No. 07/128,046, field Dec. 3, 1987 and now abandoned.

FIELD OF THE INVENTION

The present invention is directed medical devices and, more particularly, to devices for accessing the circulatory system of a person or animal. The present device includes a solid introducer with surrounding catheter for accessing a surgically implanted port which is in fluid communication with a blood vessel usually a vein.

BACKGROUND OF THE INVENTION

Introduction of fluids into a patient using a catheter and insertion device is known. For intravenous infusion, the most common insertion device is a syringe with a hollow needle received in a catheter. After insertion, some blood is extracted into the syringe before the syringe is removed from the catheter and a Luer coupler on the free end of the catheter connected to a fluid delivery system. These devices do not commonly have pre or post insertion needle covers or protectors. Another known system for intravenous infusion has a flexible catheter disposed within the bore of a hollow needle. After the needle is inserted into a vein, the catheter is pushed through the hollow end of the needle as the needle is retracted. A significant drawback of this type of device is that once the insertion needle is withdrawn, the needle cannot be removed from the catheter. The Luer lock or other coupling mechanism has a diameter too large to pass through the needle bore. Since the needle cannot be removed, it is continuously present on the catheter outside the patient's body and is a continuous source of possible problems.

A separable catheter insertion device is shown in U.S. Pat. No. 3,682,173. A longitudinal slot runs the length of the needle and of the hub member secured to the needle. The slot facilitates removal of the catheter from the needle after insertion of the catheter into the patient.

In a related application, now abandoned, filed Oct. 31, 1986, having Ser. No. 925,313 and assigned to the Assignee of the present application, a splittable needle functions to emplace a catheter. Once the catheter is in place, the applicator operates to slit the needle so that it can be removed from the catheter and disposed of.

The indicated devices with hollow needles allow for the extraction or flashback of blood when the vein has been pierced. In many cases such feature is important. There is another class of cases, however, where it is not necessary. Particularly, flashback does not occur when a catheter is inserted into a previously surgically emplanted port. A port is a device which forms a reservoir with a rubberized septum on the access side nearest the skin and a solid surface on a side opposite. The port further includes a tube leading from the reservoir to a vein or other blood vessel. The device is placed under the skin to provide a bacterial covering and is placed in a location convenient to the doctor considering the intended use. A port is commonly used to administer chemotherapy, is used to advantage in areas where the veins of the patient have collapsed or collapse easily, and may be used specifically to avoid flashback and provide safety to a clinician when treating a patient, for example, with AIDS.

The syringe type and other devices mentioned above which are known and used for intravenous access are not generally appropriate for accessing a port. The catheters do not have sufficient radical strength to avoid collapse at the septum and the internal diameter is small and limited by the size needle possible considering the use.

Generally, known devices for accessing ports are hollow needles (no catheters). The problem with hollow needles is the coring of the septum produced by the tip of the needle. Because of the causticity of medicines directed into a port and thereafter the venous system, it is important that medicines not leak from the port. Any coring of the septum reduces substantially the number of times which the septum can be accessed without unacceptably increasing the risk of leakage. Furthermore, the fact of coring limits the cross-sectional size of needles which can be introduced to a port.

Thus, to summarize, known catheter insertion devices enclose a relatively flexible catheter and are primarily intended for directly accessing a bio-target, commonly a vein. Generally, port access devices are hollow needles and do not emplace catheters. With the insertional devices enclosing catheters, the catheters are necessarily small and lack compressive strength. With the port access needles, coring can be a problem. The present invention uses a solid introducer and a catheter thereover so that it is particularly suited for accessing a port and removing and covering the introducer.

SUMMARY OF THE INVENTION

The present invention is a circulatory system access apparatus which includes a port, a solid introducer, a semi-rigid catheter, and a mechanism for holding the introducer and the catheter. The solid introducer has a tip and a shaft of uniform cross-sectional shape along the distal end portion of the shaft. The catheter slidably fits about the distal portion of the shaft of the introducer. The holding mechanism holds the introducer and the catheter together during insertion through the septum into the reservoir of the port and includes pushing mechanism. The catheter is disconnected from the introducer at the holding mechanism after insertion so that the introducer may be discarded with only the catheter remaining in fluid communication with the reservoir.

The present invention is also directed to a method of using the access device which includes the steps of inserting the solid introducer while surrounded by the catheter through the skin of the person or animal and the septum of the port, and then retracting and removing the introducer from the catheter.

In further embodiments of the method, telescoping containers are locked with respect to one another before the distal ends of the introducer and catheter are exposed so that they may be inserted. In still further embodiments of the method, the introducer is axially covered by the containers as the introducer is retracted and removed from the catheter so that when the introducer is fully retracted, the telescoping containers are locked with respect to one another so that the introducer remains covered.

The access apparatus of the present invention is particularly advantageous since the introducing element is solid and the catheter surrounds it so that on insertion, there is no coring of the septum. In this way, larger catheters may be inserted. Furthermore, the lifetime of a port is substantially increased for a given introducer size. Because ports are surgically emplaced, the number of insertions for any one emplaced port or the lifetime is a critical performance parameter.

The present device is of further advantage in that a covering container mechanism is provided which not only longitudinally covers the introducer and catheter before insertion, but also covers the introducer as it is retracted from the catheter after insertion and locks the covering mechanism in place to prevent any accidental pricking prior to responsible discarding.

The present invention if of still further advantage in that one of the catheter embodiments includes a first tube of TEFLON which is relatively rigid and a second tube of polyvinylchloride (PVC) or other more flexible material with a connector therebetween. A Luer lock or other suitable coupler is attached to the other end of the second tube. In any case, during insertion the container mechanism pushes on both the needle and the connector so that force is applied to both the needle and the first tube of the catheter thereby preventing the septum from sliding the catheter along the needle rather than allowing the catheter to be inserted along with the needle. The catheter is of further advantage in that the second tube is flexible and, consequently, available for clamping. Furthermore, the flexible second tube is on the opposite side of the connector, i.e., the location at which force is being applied, so that the flexible tube does not collapse during insertion.

The present invention thusly summarized and advantages indicated may, however, be better understood by reference to the drawings briefly described hereinafter and to the detailed description of the preferred embodiment following thereafter.

BRIEF DESCRIPTION OF THE DRAWINGS

FIG. 8 is a longitudinal, cross-sectional view of the access apparatus showing in solid lines the apparatus just after removal of the locking pin and showing in broken lines the apparatus after insertion of the introducer and catheter through the septum;

FIG. 9 is a longitudinal, cross-sectional view rotated 90° with respect to the view of FIG. 8 showing the device after retraction of the introducer from the inserted catheter;

FIG. 10 is an enlarged side view of the distal end of the introducer and surrounding catheter.

FIG. 14 is a cross-sectional view of an alternate embodiment;

FIG. 15 is a cross-sectional view of a catheter after insertion relative to the guard and handle in post-insertion position;

FIG. 16 is a cross-sectional view taken along line 16—16 of FIG. 15;

FIG. 17 is a cross-sectional view taken along line 17—17 of FIG. 14; and

FIG. 18 is a cross-sectional view of the post-insertion lock mechanism.

DETAILED DESCRIPTION OF THE PREFERRED EMBODIMENT

Figures 1, 2:
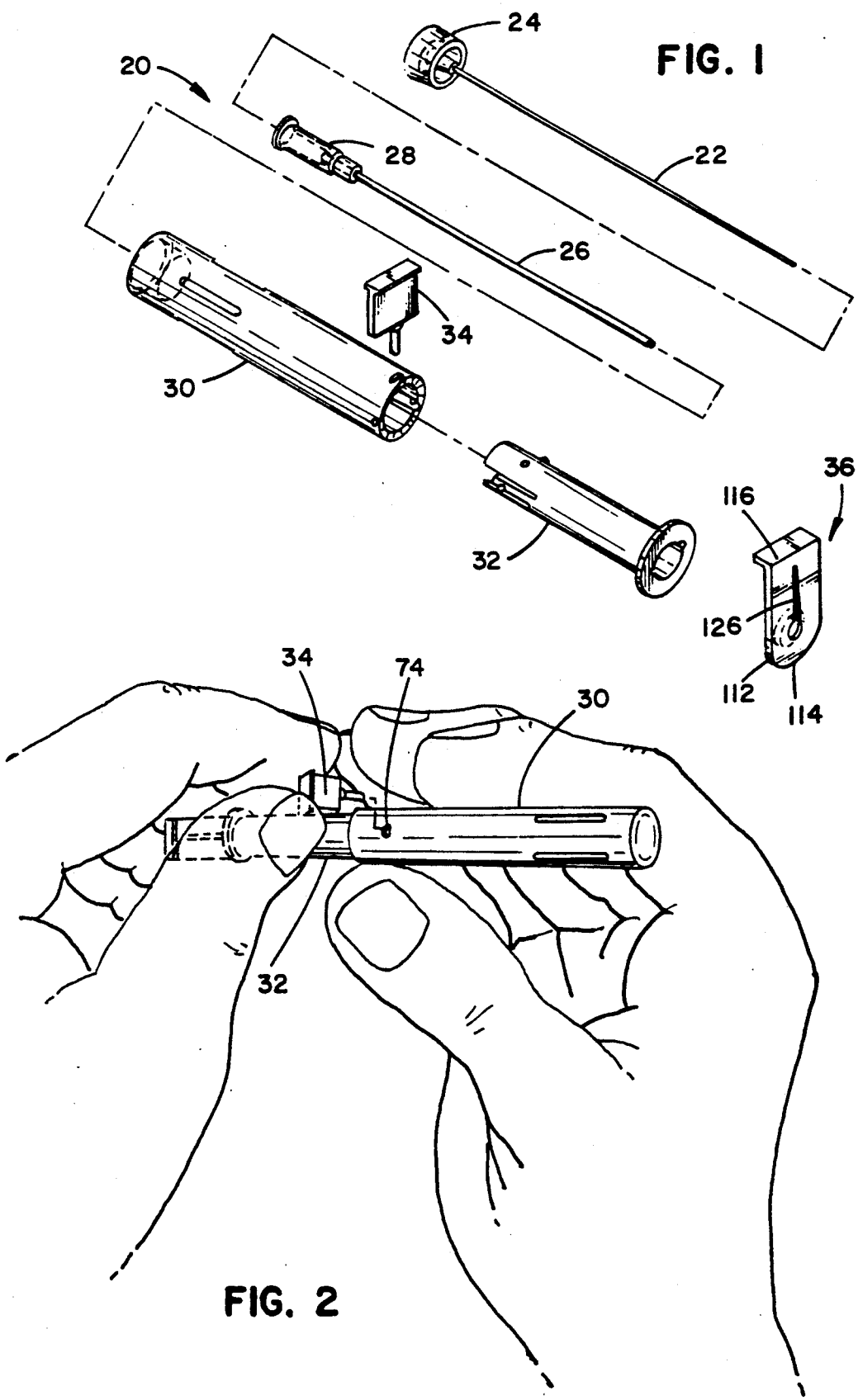
FIG. 1 is an exploded perspective view of an access apparatus in accordance with the present invention.
FIG. 2 is a perspective view of the locking pin being removed from aligned openings in the guard and handle.

Referring now to the drawings wherein like reference numerals designate identical or corresponding parts throughout the several views, and referring more particularly to FIG. 1, an access device in accordance with the present invention is designated generally by the numeral 20. Device 20 includes an introducer 22 with a hub 24. The introducer is sized to slidably, but snugly, fit within semi-rigid catheter 26 having a coupler 28, usually a Luer lock, at one end. Hub 24 is held securely at the proximal end of a first container called the handle 30. A second container, called the guard 32, telescopes into and out of handle 30. A locking pin 34 holds the handle 30 and guard 32 in a fixed relationship relative to one another during the pre-insertion. A clamp 36 for catheter is held to the end of guard 32 during pre-insertion.

With reference to FIGS. 8 and 9, a port 38 is shown after surgical emplacement beneath the skin 40 of a person or animal. Port 38 is commonly formed to have a housing 42 to include a cavity which when covered with a rubberized septum 44 encloses a reservoir 46. Housing 42 is made of a biocompatible and drug compatible material like titanium or a plastic polymer. Port 38 is oriented with septum 44 on an access side nearest the skin 40. Housing 42 then provides a solid surface 47 on a side opposite septum 44. Housing 42 has a flange 48 with a plurality of openings through which sutures 50 may be passed to tie port 38 to muscle or other tissue 52. Housing 42 further includes a passage 54 exiting reservoir 46 to a fitting 56 to which a tube 58 is fastened. Tube 58 is directed in a fashion not shown into a vein 60.

Handle 30 is preferably cylindrical and hollow. The proximal end portion 62 is formed to have a frusto-conical bore 64. A plurality of ribs 66 extend inwardly from the sidewall 68 of handle 30 at a location adjacent to bore 64. The taper of bore 64 and ribs 66 help to function to secure hub 24 of needle 22 as discussed further hereinafter. The remaining portion 70 of handle 30 is cylindrically hollow. The distal end 72 has an inwardly directed taper which aids in the assembly of guard 32 to handle 30. An opening 74 is formed in sidewall 68 near the distal end of handle 30 to receive locking pin 34.

Guard 32 preferably has a cylindrical sidewall 76. A flange 78 is formed at the distal end. A pair of cantilevering arms 80 are formed in the proximal end portion of sidewall 76. Each arm 80 includes a protrusion 82 which extends outwardly with respect to sidewall 76. Preferably, arms 80 do not extend completely to proximal end 84. It is noted that protrusion 82 extends outwardly sufficiently far to protrude through openings 86 in the distal end portion of handle 30.

Guard 32 also has an opening 88 in sidewall 76 so that when openings 74 and 88 of cover 30 and guard 32, respectively, are aligned, locking pin 34 can be inserted thereby holding the two containers in a first position which is then fixed relative to the other elements of device 20.

As shown in FIG. 9, handle 30 includes a pair of grooves 90 extending from openings 86 to ridges 66. Protrusions 82 are offset from opening 88 so that grooves 90 receive protrusions 82 when the containers are locked in the first position. When guard 32 is telescoped into handle 30 until proximal end 84 contacts ridges 66 or until flange 78 contacts the distal end of handle 30, protrusions 82 follow grooves 90 and guide the movement of the containers relative to one another. The containers are shown by the broken lines in FIG. 8 in a second position whereby guard 32 is fully telescoped into cover 30.

When guard 32 is telescoped out of cover 30, protrusions 82 again follow grooves 90. In this case, there is no locking pin or any other obstruction to stop guard 32 until arms 80 spring protrusions 82 into openings 86 to define a third position of the containers relative to one another.

Introducer 322 and catheter 26 have proximal and distal end portions with central portions therebetween. Hub 24 axially receives introducer 22 at the proximal end portion of introducer 22. Hub 24 and introducer 22 are fastened together with a medically approved adhesive or another known fashion. Hub 24 has an outer frusto-conical flange 92 which mates with bore 64 and has sufficient longitudinal length to extend approximately between ribs 64 and the proximal end of handle 30. Hub 24 also includes a central boss 94 which receives introducer 22.

Introducer 22 has a solid shaft 96 with a tip 98. Shaft 96 is preferably uniformly cylindrical. In particular, the portion of shaft 96 which extends beyond guard 32 when device 20 is in the second position, called the distal end portion, has a uniform cross-sectional shape. Tip 98, although shown conical, is preferably multi-faceted. It is clear that a variety of other tips are also appropriate.

Catheter 26 is made of a material e.g. TEFLON which has radical and longitudinal compressive strength so that the septum does not cause it to collapse during and after insertion, yet which allows bending without kinking, at the skin after insertion. Catheter 26 advantageously has a relatively large internal diameter which just receives introducer 22. The distal end 106 of catheter 26 has a taper to match the design of tip 98 of introducer 22.

The most convenient coupler fastened to the proximal end of catheter 26 is a conventional Luer lock 28. In any case, the coupler shown in FIGS. 8 and 9 includes a central cavity 100 for receiving boss 94. A flange 102 extends outwardly from the wall of cavity 100 at the proximal end of coupler 28. Catheter 26 is fastened with a medically approved adhesive or another known fashion to the body 104 of coupler 28 so that catheter 26 opens to cavity 100.

Introducer 22 and catheter 26 have longitudinal length relative to one another so that when flange 102 is fitted against hub 24 with boss 94 received in cavity 100, tip 98 and end 106 of catheter 26 mate in a consistent design such as the conical design shown. When hub 24 is received and fastened in bore 64 of handle 30, introducer 22 and catheter 26 extend beyond handle 30 to about half way along the length of guard 32 when handle 30 and guard 32 are locked in the first position. In this way, when handle 30 and guard 32 are moved to the second position, introducer 22 and catheter 26 extend beyond flange 78 of guard 32 sufficiently far to accomplish an effective insertion to port 38.

Lock pin 34 includes pin 108 fastened to a plate-like handle 110. Pin 108 has dimensions which allow it to fit into openings 74 and 88 and extend through both without interfering with catheter 26 and introducer 22 which are located approximately along the axis of handle 30 and guard 32.

Figure 11:
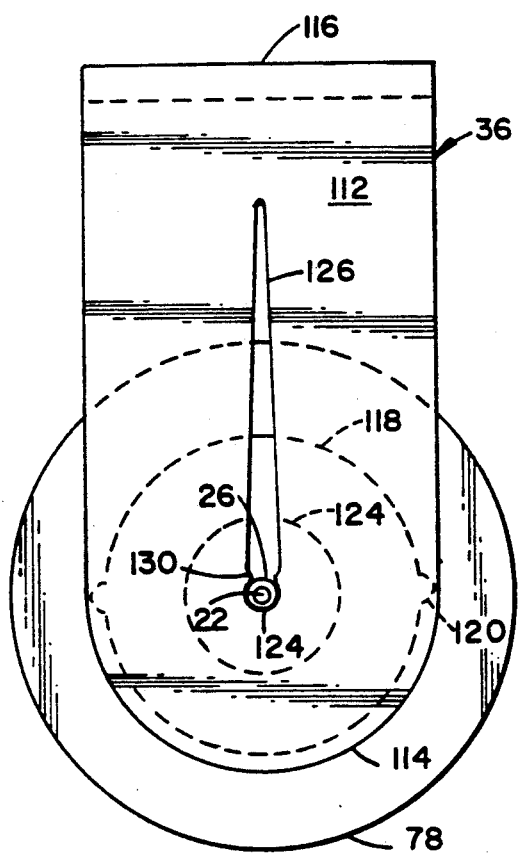
FIG. 11 is an end view of the access device taken along line 11—11 of FIG. 8.

Clamp 36 provides functions of at least partially protecting the tip of introducer 22 located within guard 32 before insertion, guiding and supporting introducer 22 and catheter 26 during insertion, and remaining on catheter 26 to provide a clamping feature for catheter 26 after insertion. Clamp 36 then has a flat member 112 and a hub 118. Flat member 112 has a semi-circular end 114 (see FIG. 1) at one end, smaller and concentric to conform to flange 78, and a handle portion which extends outwardly beyond flange 78 at the other end 116. A hub 118 is formed on flat member 112 to snugly fit into the hollow distal end of guard 32. Hub 118 includes one or more ridges 120 (see FIG. 9) along a side of hub 118. Grooves 122 are formed in the distal end of guard 32 to frictionally receive ridges 120 thereby holding clamp 36 to the end of guard 32 until moved therefrom. An opening 124 is formed along the axis of hub 118 and flairs to a greater dimension in the direction of guard 32. Opening 124 has a circular dimension only slightly greater than that of catheter 26. A slot 126 (see FIG. 1) extends toward end 116 and has an ever decreasing width as it extends away from opening 124. When catheter 26 is forced into slot 126, it functions to constrict the wall of catheter 26 and eventually clamp it closed. As shown in FIG. 11, a constriction 130 separates opening 124 from slot 126. In this way, the walls of opening 130 provide a supporting function to introducer 22 and catheter 26 as they are being pressed and forced through septum 44. Constriction 130 prevents introducer 22 and catheter 26 from bowing into slot 126.

Figure 12:
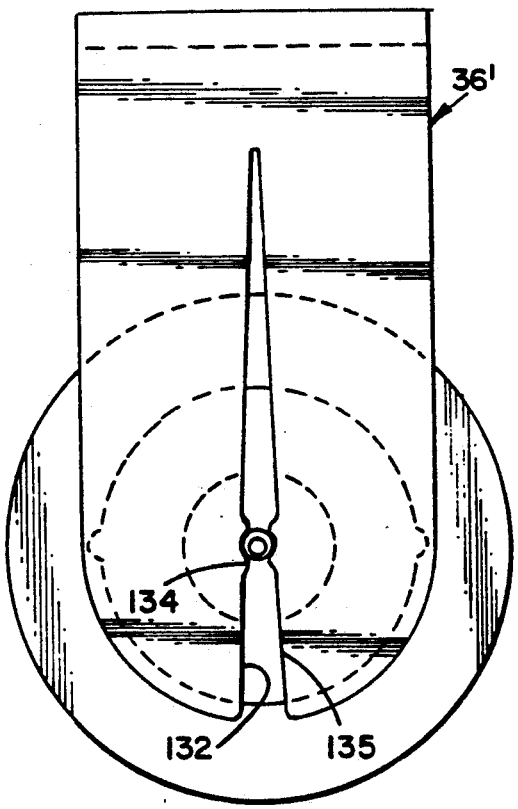
FIG. 12 is a view similar to FIG. 11 for an alternate embodiment of the catheter clamp.

In an alternate embodiment as shown in FIG. 12, equivalent elements are given equivalent numbers except they are primed. Clamp 36' is similar to clamp 36, except it includes an ever increasing slot 132 opposite from slot 126 with a second constriction 134 between opening 124 and 132. Slot 132 allows for the removal of clamp 36' from catheter 26 if it is not desired to have clamp 36' continuously attached to catheter 26. Constriction 134 has a similar size and function as constriction 130. In addition, to insure adequate support for introducer 22 and catheter 26, with this embodiment it is preferable for guard 32 to include a key 135 which fills slot 132.

Figure 13:
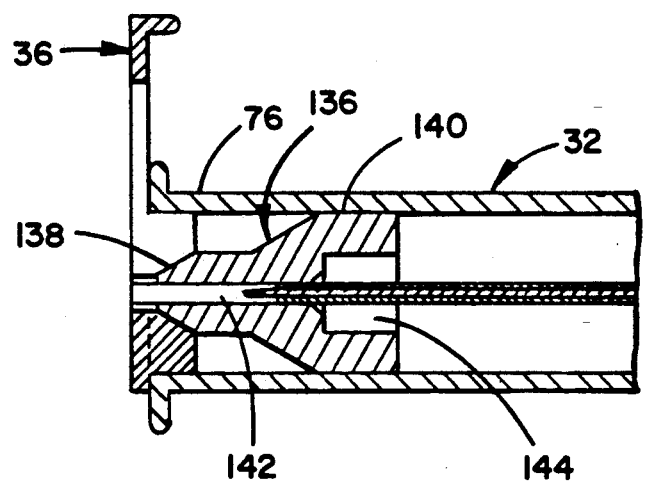
FIG. 13 is a cross-sectional view similar to FIG. 8 of a portion of the access device showing also a guide member.

Stabilizer member 136 is another mechanism for achieving support for catheter 26 and introducer 22 near the distal end of guard 32 as shown in FIG. 13. Stabilizer member 136 has a frusto-conical distal end 138 which mates with the flaired end of opening 124. The proximal end portion 140 of stabilizer member 136 extends to sidewall 76 thereby providing stability and solid support. Stabilizer member 136 includes a central opening 142 having a slightly greater dimension than catheter 26 so as to provide the desired support for the central portions of introducer 22 and catheter 26. A larger cavity 144 is formed in the proximal end portion of stabilizer member 136 so that after insertion and subsequent retraction of introducer 22, stabilizer member 136 may be moved against coupler 28 so that there is a frictional fit between the wall of cavity 144 and body 104 of coupler 28. Preferably, opening 142 is several times longer than opening 124 in clamp 36 so that when desired, stabilizer member 136 provides substantially more support for shaft 22 and catheter 26 than does clamp 36.

The method of using apparatus 20 is depicted in the illustrations of FIGS. 2-7. In general, the concept of apparatus 20 is to insert a solid introducer axially surrounded by a catheter through the skin of the person or animal and the septum of the port. Thereafter, the introducer is retracted and removed from the catheter so that the catheter remains as emplaced through the skin and septum. Additional fluid mechanism can then be connected to coupler 28 and metered through coupler 28 and catheter 26 to the reservoir 46 of port 38.

Figure 3:
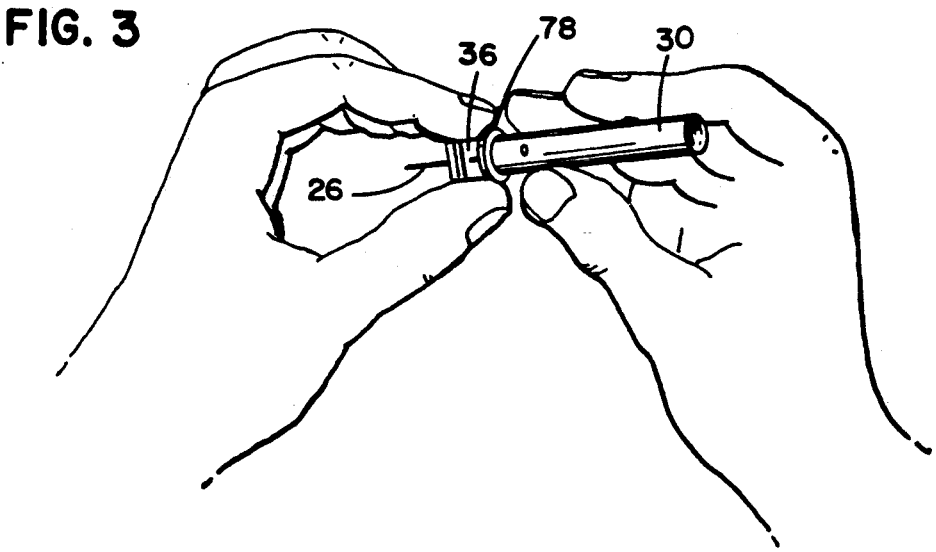
FIG. 3 is a perspective view of the guard being telescoped into the handle to expose the distal ends of the introducer and catheter.
Figure 4:
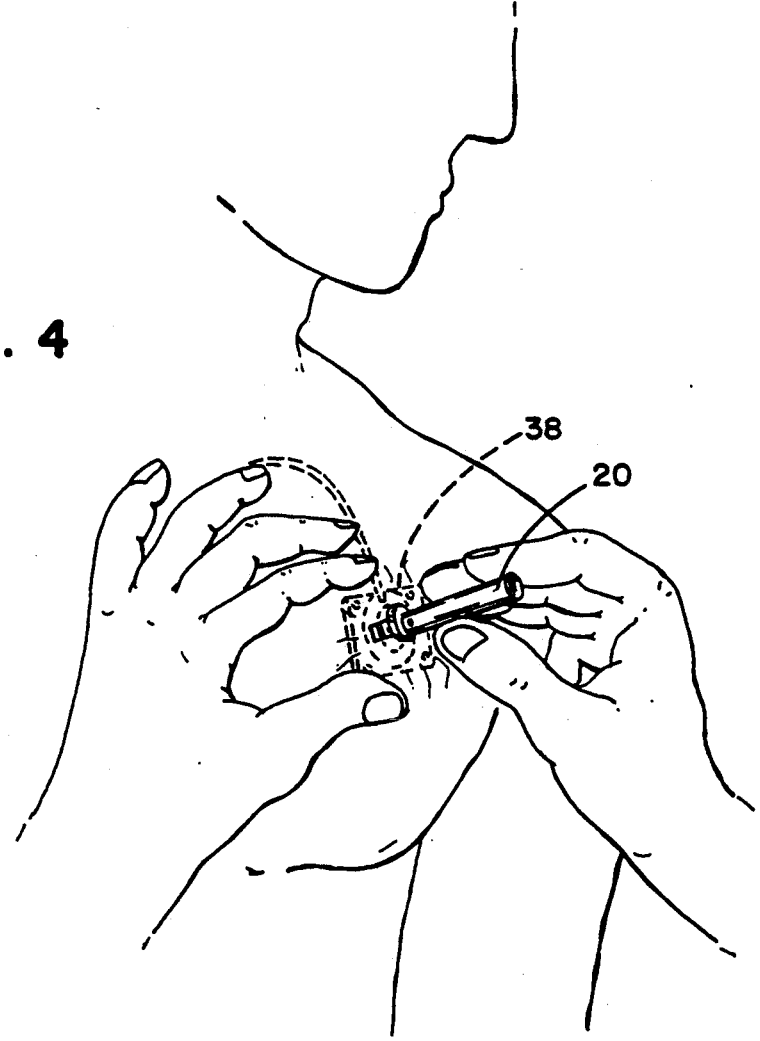
FIG. 4 is a perspective view showing insertion of the introducer and catheter into a port emplaced in the chest of a person.
Figure 5:
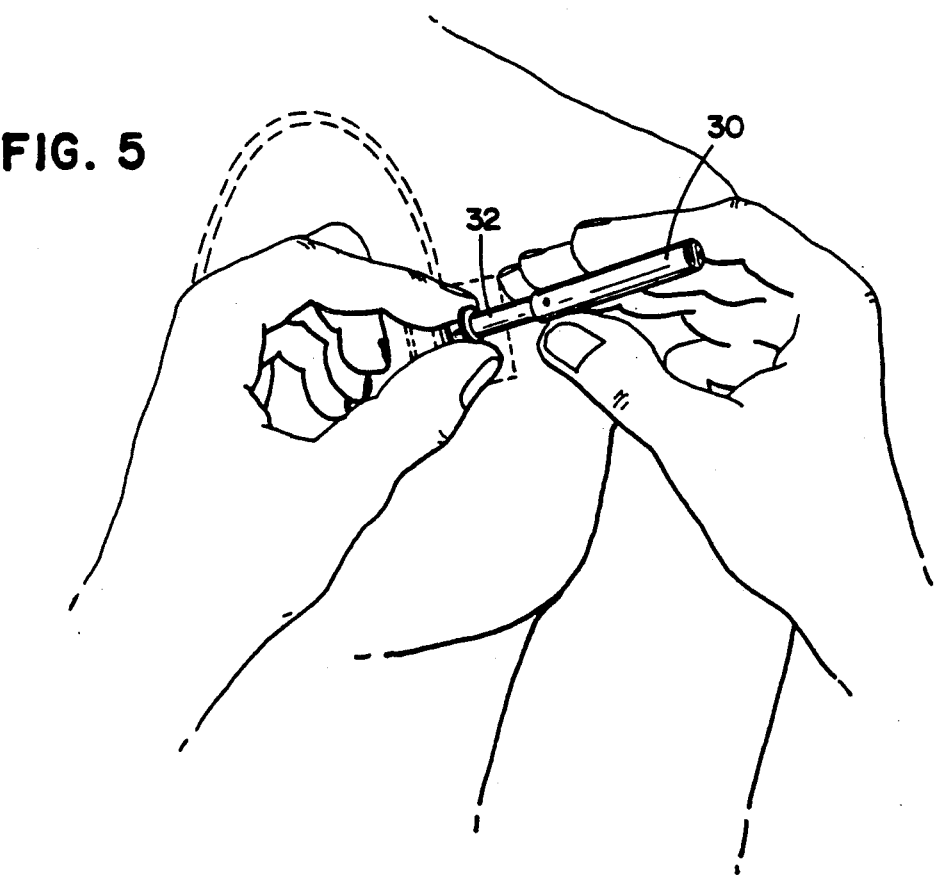
FIG. 5 is a perspective view of the guard telescoping out of the handle to protect the introducer as it is being retracted.
Figure 6:
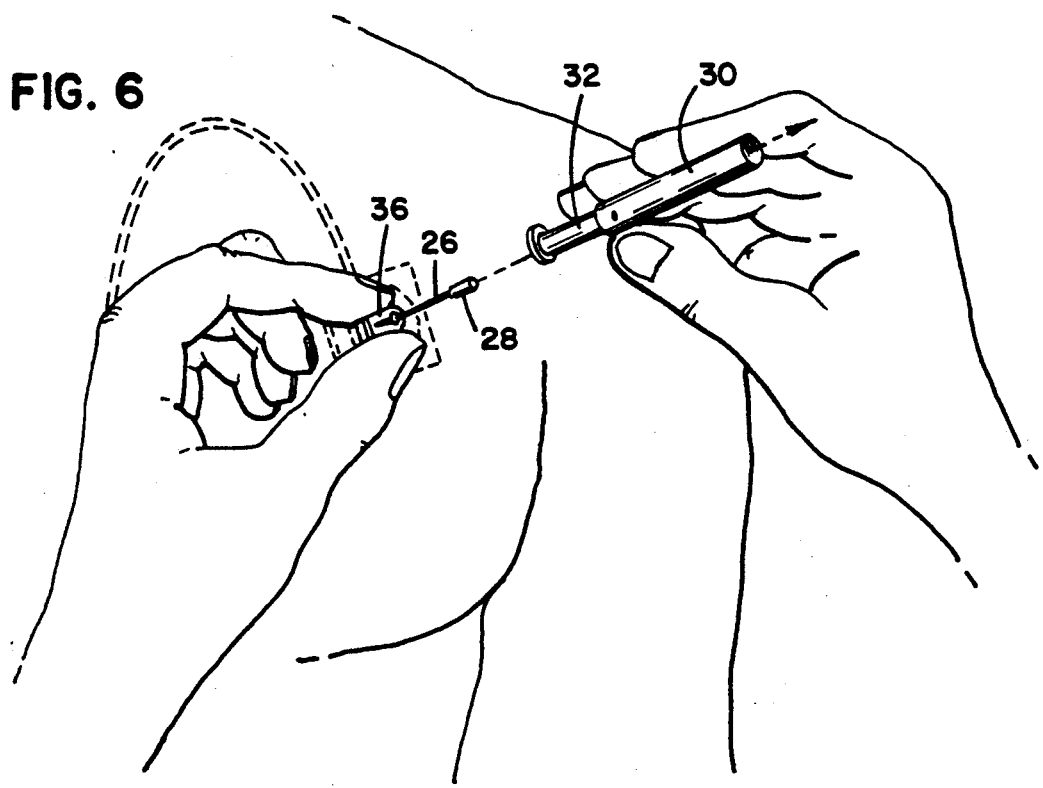
FIG. 6 is a perspective view of the covering containers being removed from the catheter with the catheter clamp remaining on the catheter.
Figure 7:
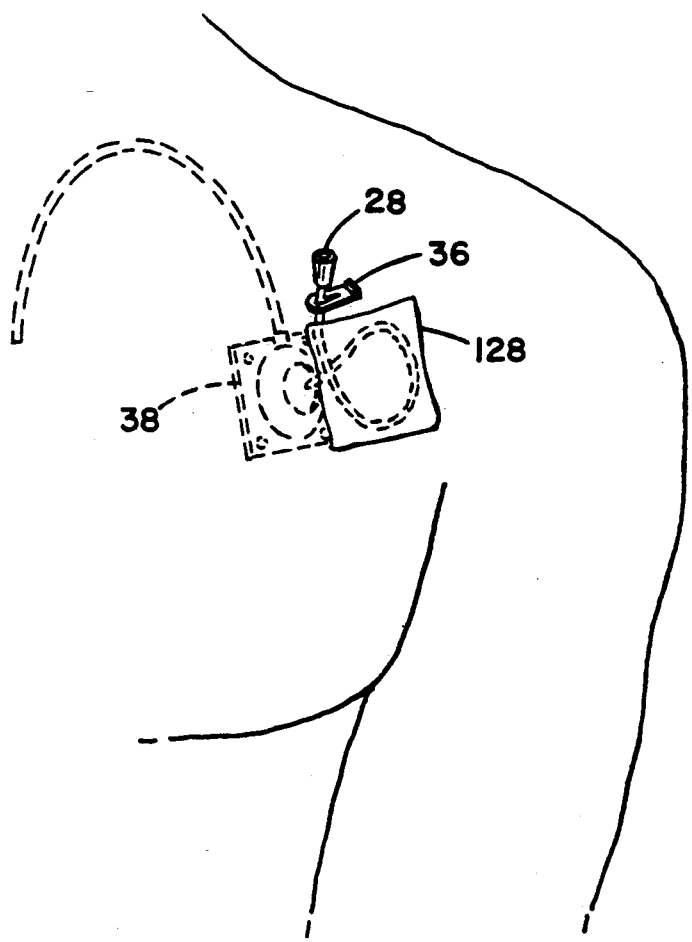
FIG. 7 is a perspective view showing the inserted catheter with respect to the emplanted port.

More particularly, as shown in FIG. 2, handle 30 and guard 32 are unlocked with respect to one another by removing locking pin 34 from openings 74 and 88. Locking pin 34 may be discarded as it has no further function. As shown in FIG. 3, guard 32 is telescoped into handle 30 by holding handle 30 in one hand by holding clamp 36 or flange 78 in the other hand and pushing guard 32 into handle 30. This movement exposes the distal end portions of introducer 22 and catheter 26. Before inserting the catheter and introducer, the skin in the vicinity of port 38 is palpated to find the rim of port 38. The catheter and introducer are then held at approximately a 90° angle with respect to the skin and inserted through the skin and the septum. Apparatus 20 is forced toward the body until tip 98 reaches the bottom of reservoir 46. As shown in FIG. 5, retraction of introducer 22 back into a covering configuration by handle 30 and guard 32 is accomplished by holding guard 32 in a relatively fixed relationship with respect to the skin and pulling back on the handle with the free hand. The catheter 26 will be held by the strong frictional force developed between the catheter and the septum. That force is more than sufficient to overcome any smaller frictional force which may be developed between introducer 22 and catheter 26 and between coupler 28 at cavity 100 and boss 94. Thus, catheter 26 and coupler 28 will remain relatively stationary, while introducer 22 will be retracted from catheter 26 as handle 30 is moved away from the patient. As illustrated in FIG. 6, when handle 30 has been moved sufficiently far, arms 80 will force protrusions 82 into openings 86 to lock handle 30 and guard 32 in the third position relative to one another so that introducer 22 is longitudinally surrounded by the containers. Clamp 36 is pulled from the distal end of guard 32, and introducer 22, handle 30 and guard 32 are separated from catheter 26 and coupler 28. Clamp 36 remains on catheter 26 between coupler 28 and the skin of the patent as shown in FIG. 7. A dressing 128 may be used to hold catheter 26 to the skin of the patient thereby providing a strain relief for catheter 26 with respect to port 38.

An alternate embodiment of the access device in accordance with the present invention is shown in FIGS. 14-18 and is designated generally by the numeral 20″. Device 20″ includes an introducer 22″ with a hub 24″. The introducer fits within a catheter 26″. The hub 24″ which holds introducer 22″ is held securely at the proximal end of handle 30″. Guard 32″ telescopes into and out of handle 30″. During pre-insertion, a locking pin (not shown) similar to locking pin 34 holds the handle 30″ and guard 32″ in a fixed relationship.

Catheter 26″ includes first and second tubes 150 and 152 with a connector 154 therebetween. First tube 150 is less flexible than second tube 152. First tube 150 is preferably made from a material like TEFLON which will hold radial and compressive rigidity to the extent necessary when forcing the introducer and tube through a septum and remaining therein. Second tube 152 is preferably made from a resilient material like polyvinylchloride (PVC) of a type which can be collapsed in a clamping fashion and when released, will retain memory of its original shape. A catheter having both a semi-rigid tube and a flexible tube serves both the purpose of making insertion in the desired environment possible and also the purpose of clamping so that the catheter need not ever be open. It is desirable to clamp the catheter, for example, when removing one type of fluid and installing a second. Also, the present catheter can be made of a short length and when other fluid systems are removed, blood may be drawn if desired.

Connector 154 provides a connecting function between the less flexible tube 150 and the more flexible tube 152. Each tube has different internal and external diameters, and the connector 154 has appropriate bosses and passages for receiving each. In particular, first tube 150 is inserted and fastened within an axial passage 156 which extends the longitudinal length of connector 154. Flexible tube 152 fits over boss 158 located at the proximal end of connector 154. Connector 154 is formed to have wing members 160 which extend transversely with respect to handle 30″. Wing member 160 has sufficient thickness and sufficient length to provide sufficient structure to receive the force of handle 30″ and adequately support and pass along sufficient force to first tube 150 during insertion.

Catheter 26″ includes a Luer lock or other appropriate coupler 28″ at the proximal end of flexible tube 152. Medically approved adhesives are used to fasten couple 28″ and connector 154 to first and second tubes 150 and 152.

Handle 30″ is cylindrical and hollow. The proximal end portion 62″ is formed to have a frustoconical bore 64″ to receive hub 24″. A plurality of ribs 162 extend from bore 64″ toward the distal end of handle 30″ to a location where the distal end 164 contacts the proximal ends 166 of wing member 160 when coupler 28″ is received on the boss 94″ of hub 24″. Ribs 162 extend transversely inwardly sufficiently far so as to contact wing member 160 which extends transversely outwardly from the axis of handle 30″. Ribs 162 are spaced apart sufficiently far so that coupler 28″ can pass between them.

Guard 32″ is cylindrical and includes a stabilizer member 136″ at the distal end. Stabilizer member 136″ is removable from guard 32″ and is split so that it falls away from catheter 26″ when it is removed from guard 32″. Handle 30″ and guard 32″ include openings for cooperation with a locking pin to hold the containers in the pre-insertion position.

With respect to the post-insertion locking mechanism, guard 32″ includes a relatively, circumferentially short flange 168 (see FIG. 18) on opposite sides of guard 32″. Handle 30″ has U-shaped channels formed along opposite sides extending from at least the distal end of wing member 160 to the distal end of handle 30". Short flanges 168 are guided along channels 170 in the same fashion that protrusions 82 follow grooves 90 with respect to device 20. Handle 30" includes arms 80" cut in each outer wall of channels 170. Arms 80" are cantilevered from the more proximal end. Near the distal end, each arm includes a ramp 172 extending inwardly and toward the distal end. A groove 174 follows ramp 172. The distal side of groove 174 is formed by a wall 176. As guard 32" is slid from the second position as described with respect to device 20, toward the third position, flanges 168 cam arm 80" outwardly as flanges 168 move along ramps 172. When flanges 168 are received in grooves 174, guard 32" and handle 30" are locked with respect to one another in the third position.

Preferably, channels 170 are oriented 90 degrees with respect to wing member 160. Such orientation is achieved by an appropriate pair of notches in coupler 28" which receive protrusions 178 extending from hub 24" (see FIG. 17).

The method of use of access device 20" is similar to device 20 and need not be further described.

Thus, a preferred and alternate embodiment and method of using the invention have been described in detail and advantages of structure and function have been set forth. It is understood, however, that equivalents are possible. Therefore, it is understood that changes made in the structure and the use of the disclosed invention, especially in matters of shape size and arrangement, to the full extent extended by the general meaning of the terms of which the appended claims are expressed, are intended to be within the principle of the present invention.

What is claimed is:

1. A transcutaneous infusion apparatus, comprising:
an implantable infusate injection port including a housing forming a reservoir with a self-sealing septum on an access side and solid surface on a side opposite, said port having an outlet tube, said port being adapted for implantation in a human or animal body with the septum located under the skin and the outlet tube leading to an infusion site in the body;
a solid needle having first distal and proximal end portions, said needle having a tip and a shaft along the distal end portion;
catheter means for accessing said port, said catheter means including a first tube of a less flexible material forming a distal end portion and a second tube of a more flexible material with a coupler attached thereto forming a proximal end portion and a connector fastened between said first and second tubes, said first tube slidably fitting about the distal end portion of the shaft of said needle, said connector including wing members extending transversely with respect to said first and second tubes;
a handle container having a proximal end attached to said needle, said handle container also having a distal end, said handle container further including a transversely extending surface for contacting said wing members;
a guard container telescopically fitting within the distal end of said handle container, said handle container and said guard container having a first position longitudinally surrounding said needle and said catheter means, said guard container formed to telescope into said handle container to a second position which is suitable for insertion of said needle and said catheter means into the septum of said port; and
means for locking said handle container and said guard container in a third position to longitudinally surround said needle during retraction of said needle from said catheter means after insertion.

2. A transcutaneous infusion apparatus, comprising:
an implantable infusate injection port including a housing forming a reservoir with a self-sealing septum on an access side and solid surface on a side opposite, said port having an outlet tube, said port being adapted for implantation in a human or animal body with the septum located under the skin and the outlet tube leading to an infusion site in the body;
a longitudinally-extending needle;
catheter means for accessing the reservoir of said port, said catheter means having a part fitting about a portion of said needle, said catheter means including a first tube of a less flexible material and a second tube of a more flexible material with a connector connecting said first an second tubes together, said first tube proximal said port during insertion and said second tube distal said port during insertion, said catheter means also including a coupler at an end of said second tube opposite said container, said needle passing through said coupler to separate a holding means from said catheter means; and
means for holding said needle and said catheter means in order to insert said needle and said catheter means through said septum, said holding means having a distal end portion spaced from said port during insertion and a proximal end portion adjacent said port during insertion, said holding means including means for pushing said needle and said catheter means during insertion, said pushing means located in said distal end portion of said holding means, said holding means also including means for radially stabilizing said needle and said catheter means in said proximal end portion of said holding means, said radially stabilizing means allowing said catheter means to be separated from said holding means after insertion, said holding means further including a longitudinal wall extending between and supporting said pushing means and said stabilizing means.

3. A transcutaneous infusion apparatus, comprising:
an implantable infusate injection port including a housing forming a reservoir with a self-sealing septum on an access side and solid surface on a side opposite, said port having an outlet tube, said port being adapted for implantation in a human or animal body with the septum located under the skin and the outlet tube extending to an infusion site in the body;
a longitudinally-extending needle;
catheter means for accessing the reservoir of said port, said catheter means having a part fitting about a portion of said needle;
means for holding said needle and said catheter means in order to insert said needle and said catheter means through said septum, said holding means having a distal end portion spaced from said port during insertion and a proximal end portion adjacent said port during insertion, said holding means including means for pushing said needle and said catheter means during insertion, said pushing means located in said distal end portion of said holding means, said holding means also including means for radially stabilizing said needle and said catheter means in said proximal end portion of said holding means, said radially stabilizing means allowing said catheter means to be separated from said holding means after insertion, said holding means further including a longitudinal wall extending between and supporting said pushing means and said stabilizing means; and said catheter means including means for contacting said pushing means and means for connecting to an accessory device and tubular means for resiliently collapsing therebetween in order to prevent fluid flow, said needle passing through said connecting means to separate said holding means for said catheter means.

4. Apparatus in accordance with claim 3 wherein said catheter means further includes a first tube of less flexible material forming a second distal end portion, said resilient collapsing means including a second tube of more flexible material, said contacting means including a connector connecting said first and second tubes together.

5. Apparatus in accordance with claim 4 wherein said contacting means further includes wing members on said connector so that said wing members can be pushed by said pushing means.

6. A transcutaneous infusion apparatus, comprising:
an implantable infusate injection port including a housing forming a reservoir with a self-sealing septum on an access side and solid surface on a side opposite, said port having an outlet tube, said port being adapted for implantation in a human or animal body with the septum located under the skin and the outlet tube extending to an infusion site in the body;
a longitudinally-extending needle;
catheter means for accessing the reservoir of said port, said catheter means having a part fitting about a portion of said needle; and
means for holding said needle and said catheter means in order to insert said needle and said catheter means through said septum, said holding means including first and second hollow containers such that one of said first and second containers telescopes longitudinally into and out of the other, said first container being attached to said needle and including means for pushing said needle and said catheter means during insertion, said second container including means for radially stabilizing said needle and said catheter means at an end of said second container proximal the insertion site during insertion, said radially stabilizing means allowing said catheter means to be separated from said holding means after insertion, said containers having a first position with respect to one another wherein said containers longitudinally surround said needle and said catheter means, said containers having a second position with respect to one another wherein said needle and said catheter means extend out one end of said first and second containers, said containers having a third position with respect to one another wherein said containers longitudinally surround said needle.

7. Apparatus in accordance with claim 6 wherein said catheter means includes a longitudinal tube surrounding said needle and a first transversely extending member attached to said tube, wherein said first container is more distal and said second container is more proximal, said second container having a side wall, and wherein said pushing means includes a second transversely extending member as a portion of said second container, said second transversely extending member contacting said first transversely extending member for pushing said first transversely extending member.

8. Apparatus in accordance with claim 7 wherein said holding means includes means for aligning said first and second transversely extending members with respect to one another.

9. The apparatus in accordance with claim 8 wherein said catheter means includes central portions, said first container having a sidewall and a distal end portion, said apparatus further including an end member having a wall in contact with the side wall along the distal end portion of the first container, said send member also having an opening only slightly larger than said needle and said catheter to stabilizer the central portions of said needle and said catheter during insertion.

10. The apparatus in accordance with claim 8 wherein said holding means further includes first means for locking said first and second containers in said first position before insertion.

11. The apparatus in accordance with claim 19 wherein said first locking means includes a first opening in said first container and a second opening in said second container, said first and second openings being alignable, said first locking means further including a pin extending into said first and second openings to hold said first and second containers in said first position.

12. The apparatus in accordance with claim 10 wherein said holding means further includes second means for locking said first and second containers in said third position.

13. The apparatus in accordance with claim 12 wherein said first container includes a first sidewall and said, second container includes a second sidewall, said second locking means including one of said first and second sidewalls having a cavity with spaced apart edges and the other of said first and second sidewalls having means for engaging said edges.

14. The apparatus in accordance with claim 13 wherein said engaging means includes an arm cantilevered from said other of said first and second sidewalls, said arm having a protrusion extending therefrom to engage said edges.

15. The apparatus in accordance with claim 14 wherein said holding means also includes means for guiding said second container with respect to said first container from said first position to said second position to said third position.

16. The apparatus in accordance with claim 15 wherein said guiding means includes a groove in the first sidewall of said first container for receiving the protrusion on the arm extending from the second sidewall of said second container.

* * * * *

UNITED STATES PATENT AND TRADEMARK OFFICE
CERTIFICATE OF CORRECTION

PATENT NO. : 5,135,502
DATED : August 4, 1992
INVENTOR(S) : Marvin E. Koenig, Jr. et al.

It is certified that error appears in the above-identified patent and that said Letters Patent is hereby corrected as shown below:

Col. 1, line 11, insert --generally to-- before "medical" and after "directed".

Col. 5, line 30, "322" should be --22--.

Col. 12, line 25, "stabilizer" should be --stabilize--.

Col. 12, line 31, "19" should be --10--

Col. 10, line 27, "container" should be --connector--.

Signed and Sealed this

Eighteenth Day of January, 1994

BRUCE LEHMAN

*Attest:*

*Attesting Officer*    Commissioner of Patents and Trademarks